(12) United States Patent
Peyton et al.

(10) Patent No.: US 10,144,987 B2
(45) Date of Patent: Dec. 4, 2018

(54) SENSORS

(71) Applicant: THE UNIVERSITY OF MANCHESTER, Manchester (GB)

(72) Inventors: Anthony Joseph Peyton, Bolton (GB); Wuliang Yin, Manchester (GB); Stephen John Dickinson, Lancaster (GB)

(73) Assignee: THE UNIVERSITY OF MANCHESTER, Manchester (GB)

( * ) Notice: Subject to any disclaimer, the term of this patent is extended or adjusted under 35 U.S.C. 154(b) by 74 days.

(21) Appl. No.: 15/177,953

(22) Filed: Jun. 9, 2016

(65) Prior Publication Data

US 2016/0289789 A1 Oct. 6, 2016

Related U.S. Application Data

(63) Continuation of application No. 14/114,006, filed as application No. PCT/GB2012/050930 on Apr. 27, 2012, now Pat. No. 9,404,992.

(30) Foreign Application Priority Data

Apr. 27, 2011 (GB) .................................. 1107064.6

(51) Int. Cl.
*C21D 8/12* (2006.01)
*G01R 33/028* (2006.01)
(Continued)

(52) U.S. Cl.
CPC ............ *C21D 11/005* (2013.01); *B21B 37/76* (2013.01); *C21D 8/12* (2013.01); *G01N 27/80* (2013.01);
(Continued)

(58) Field of Classification Search
CPC ........ C21D 11/00; C21D 11/005; C21D 8/12; C21D 2211/00; B21B 37/76; G01R 35/00;
(Continued)

(56) References Cited

U.S. PATENT DOCUMENTS 4,091,322 A 5/1978 Stankoff
4,752,733 A 6/1988 Petr et al.
(Continued)

FOREIGN PATENT DOCUMENTS

CN 1059029 A 2/1992
CN 1741866 A 3/2006
(Continued)

OTHER PUBLICATIONS

Yin, W. et al., "Analysis of the Lift-off Effect of Phase Spectra for Eddy Current Sensors," IMTC 2005—Instrumentation and Measurement Technology Conference, Ottawa, Canada, May 17-19, 2005, pp. 1779-1784.
(Continued)

*Primary Examiner* — Son Le
(74) *Attorney, Agent, or Firm* — Faegre Baker Daniels LLP

(57) ABSTRACT

Embodiments of the present invention provide an electromagnetic sensor (400) for detecting a microstructure of a metal target, comprising: a magnetic device (410, 420) for providing an excitation magnetic field; a magnetometer (430) for detecting a resultant magnetic field induced in a metal target; and a calibration circuit (450, 551, 552, 553, 554) for generating a calibration magnetic field for calibrating the electromagnetic sensor, wherein the calibration reference magnetic field is generated by an electrical current induced in the calibration circuit by the excitation magnetic field.

11 Claims, 5 Drawing Sheets

(51) Int. Cl.
*G01N 27/80* (2006.01)
*C21D 11/00* (2006.01)
*G01N 33/20* (2006.01)
*G01R 33/12* (2006.01)
*G01R 35/00* (2006.01)
*B21B 37/76* (2006.01)

(52) U.S. Cl.
CPC ........... *G01N 33/20* (2013.01); *G01R 33/028* (2013.01); *G01R 33/1223* (2013.01); *G01R 35/005* (2013.01); *C21D 2211/00* (2013.01)

(58) Field of Classification Search
CPC ................ G01R 35/005; G01R 33/028; G01R 33/1223; G01R 33/0283; G01R 33/0286; G01N 33/20; G01N 27/80; G01N 2201/127
See application file for complete search history.

(56) References Cited

U.S. PATENT DOCUMENTS

| | | | |
|---|---|---|---|
| 5,329,561 | A | 7/1994 | Desruelles |
| 5,420,518 | A | 5/1995 | Schafer, Jr. |
| 6,437,573 | B1 | 8/2002 | Golder et al. |
| 6,750,644 | B1 | 6/2004 | Berkcan |
| 2002/0043976 | A1 | 4/2002 | Holladay, III et al. |
| 2003/0144820 | A1 | 7/2003 | Sakagami |
| 2009/0072815 | A1 | 3/2009 | Kahlman et al. |

FOREIGN PATENT DOCUMENTS

| | | |
|---|---|---|
| CN | 101427157 A | 5/2009 |
| EP | 0177626 | 4/1986 |
| EP | 0178378 | 4/1986 |
| EP | 0873799 | 10/1998 |
| EP | 1308721 | 5/2003 |
| EP | 1637898 | 3/2006 |
| EP | 1783487 | 5/2007 |
| EP | 1933161 | 6/2008 |
| FR | 2417102 | 10/1997 |
| GB | 1385198 | 2/1975 |
| GB | 1501751 | 2/1978 |
| JP | S50104754 | 8/1975 |
| JP | S55155265 | 12/1980 |
| JP | 60017350 | 1/1985 |
| JP | S61-175562 A | 8/1986 |
| JP | 06-325253 | 10/1988 |
| JP | 3134555 | 6/1991 |
| JP | 03-262957 | 11/1991 |
| JP | H05149923 | 6/1993 |
| JP | H07-270383 A | 10/1995 |
| JP | 07-325067 | 12/1995 |
| JP | 2000-304725 | 11/2000 |
| JP | 2008-185436 A | 8/2008 |
| KR | 20070072526 A | 10/2007 |
| SU | 1029070 A1 | 7/1983 |
| UA | 65098 U | 11/2011 |
| WO | 2006042839 | 4/2006 |
| WO | WO 2007 088502 | 8/2007 |
| WO | WO 2007 122542 | 11/2007 |
| WO | WO 2009 151449 | 12/2009 |
| WO | WO 2012 146930 | 11/2012 |

OTHER PUBLICATIONS

Dickinson et al., "The Development of a Multifrequency Electromagnetic Instrument for Monitoring the Phase Transformation of Hot Strip Steel", IEEE Transactions on Instrumentation and Measurement, vol. 56, No. 3, 2007, pp. 879-886.
Yin et al., "Exploring the relationship between ferrite fraction and morphology and the electromagnetic properties of steel", Journal of Material Science, 2007, vol. 42, pp. 6854-6861.
Yin, W. et al., "Measurement of permeability and ferrite/austenite phase fraction using a multi-frequency electromagnetic sensor," *Science Direct*, NDT&E International 42 (2009) 64-68, www.elsevier.com/locate/indteint.
Examination Report issued in application GB1107064.6, dated Dec. 2, 2011, 3 pages.
Search Report for claims 1-27 issued in application GB1107064.6, dated Aug. 4, 2011, 2 pages.
Search Report for claims 28-40 issued in application GB1107064.6, dated Aug. 4, 2011, 2 pages.
Search Report issued in application GB1205896.2, dated May 1, 2012, 2 pages.
International Preliminary Report on Patentability in related application PCT/GB2012/050930, dated Oct. 29, 2013, 13 pages.
International Search Report and Written Opinion issued in related application PCT/GB2012/050930, dated Mar. 5, 2013, 18 pages.
Decision to Grant, RU 2013152616, dated Mar. 17, 2016.
A.J. Peyton, W. Yin, S. J. Dickinson, C.L. Davis, M. Strangwood, X. Hao, A. J. Douglas & P.F. Morris (2010) Monitoring microstructure changes in rod online by using induction spectroscopy, Ironmaking & Steelmaking, 37:2, 135-139, DOI: 10.1179/030192309X12506804200861; 6 pages.
Japanese Office Action issued by the Japanese Patent Office, dated Jul. 25, 2017, for Japanese patent application No. JP 2016-179316; 3 pages.
English translation of Japanese Office Action issued by the Japanese Patent Office, dated Jul. 25, 2017, for Japanese patent application No. JP 2016-179316; 3 pages.
Extended Search Report issued by the European Patent Office, dated May 24, 2016, for European patent application No. 17164269.7-1554; 11 pages.
Notice of Allowance dated Oct. 18, 2018 for corresponding South Korean Patent Application No. 10-2013-7031396, 3 pages.

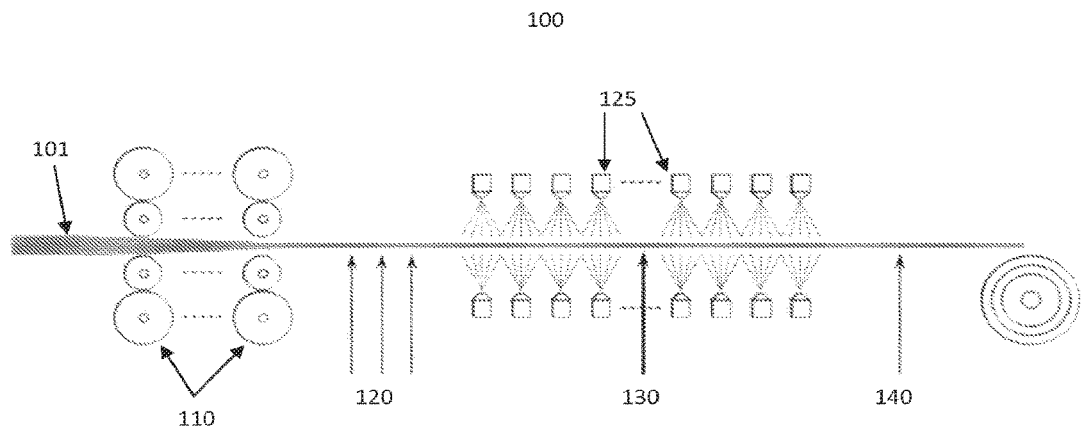
Fig. 1
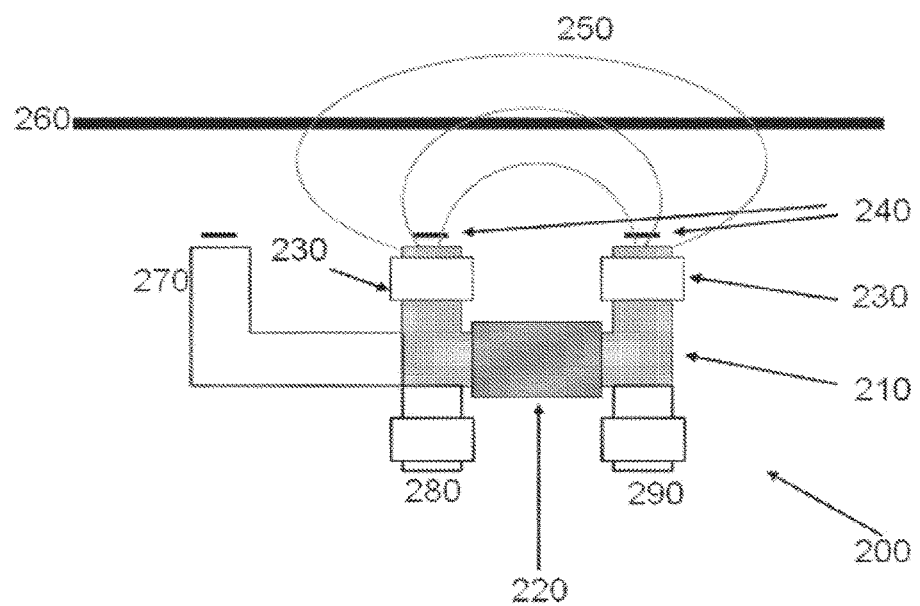
Fig 2  --Prior Art--

SENSORS

The present application is a continuation of U.S. application Ser. No. 14/114,006, filed on Oct. 25, 2013, which is a National Stage of International Application No. PCT/GB2012/050930, filed Apr. 27, 2012, which claims priority to GB 1107064.6, filed Apr. 27, 2011, the entire disclosures of which are hereby expressly incorporated herein by reference.

Embodiments of the present invention relate to apparatus and methods for monitoring the microstructure of a metal target. In particular, although not exclusively, some embodiments of the present invention relate to apparatus and methods for calibrating electromagnetic sensors. In particular, although not exclusively, some embodiments of the invention relate to monitoring the microstructural formation of a metal target.

BACKGROUND

During production processing of metals, such as steel, rolling of the metal is followed by controlled cooling. During the production processing, particularly the cooling process, a microstructure of the metal evolves and results in a final microstructure of the processed metal. The microstructure of the processed metal has an impact on many aspects of the metal's character, such as tensile strength.

Conventional microstructural analysis techniques are destructive and involve removing samples for analysis from, for example, the end of a coil of the processed material. This is time-consuming, costly, does not allow continuous monitoring, and assesses only a small fraction of the material processed.

When the processed material is steel, it is known that electromagnetic techniques can monitor steel phase transformations by detecting the ferromagnetic phase change due to the changes in electrical conductivity and magnetic permeability within the steel. Furthermore, if a coil is placed in the vicinity of the steel being processed, this results in a change in impedance measurements for the coil because conductivity and permeability are influenced by the steel's microstructure. For example austenite, the stable phase of iron at elevated temperatures, is paramagnetic whereas the stable low temperature phases ferrite, pearlite, bainite and martensite are ferromagnetic below the Curie temperature of about 760° C. Steel properties vary strongly with the volume fractions of these phases, which are controlled largely by the cooling rate and alloy content of the steel.

However, problems exist in monitoring in real-time the electromagnetic properties of metals during processing. Many problems result from the environmental conditions associated with metal processing, such as heat, moisture, humidity, etc.

It is an object of embodiments of the invention to at least mitigate one or more of the problems of the prior art.

SUMMARY OF THE INVENTION

According to aspects of the invention, there is provided apparatus and methods as defined in the appended claims.

According to an aspect of the invention there is provided an electromagnetic sensor for detecting a microstructure of a metal target, comprising: a means for providing a magnetic field; a magnetometer for detecting a magnetic field induced in a metal target; and a calibration circuit for generating a reference magnetic field for calibrating the sensor unit.

The electromagnetic sensor may comprise a plurality of calibration circuits. Each of the plurality of calibration circuits may be arranged to generate a magnetic field at a respective frequency range. Each of the plurality of calibration circuits may comprise a respective impedance. One or more calibration circuits may comprise a calibration coil. The electromagnetic sensor may comprise a control means for selectively controlling the generation of the reference magnetic field. The reference magnetic field may be generated by an electrical current induced in the calibration circuit by the magnetic field. The magnetometer may be an induction detector coil or a Hall sensor.

The electromagnetic sensor may comprise a magnetic core. The magnetic core may be U-shaped or H-shaped. The magnetometer may be arranged proximal to a pole of the core. The means for generating the magnetic field may comprise one or more excitation coils. The electromagnetic sensor may comprise a control unit arranged to determine a calibration period and to selectively activate the calibration circuit during the calibration period. The control unit may be arranged to determine the calibration period based upon a detection signal output from the magnetometer. The control unit may be arranged to determine calibration period based on the detection signal output from the magnetometer and a predetermined reference level. The control unit may comprise an input for receiving a signal from a production apparatus indicative of a period between metal targets, wherein the control unit is arranged to determine the calibration period based thereon. The control unit may be arranged to selectively control a plurality of calibration circuits. The control unit may be arranged to cause each of the plurality of calibration circuits to output a respective frequency.

According to an aspect of the invention there is provided a method of calibrating an electromagnetic sensor, comprising: providing an excitation magnetic field; causing a calibration circuit to output a calibration magnetic field; receiving a resultant magnetic field at one or more magnetometers; and determining a calibration of the electromagnetic sensor based on the resultant magnetic field.

The excitation magnetic field may include a multi-frequency waveform. The method may comprise causing a plurality of calibration circuits to each output a calibration magnetic field at a respective frequency range, and determining the calibration of the magnetic sensor at each respective frequency range. The method may comprise determining a phase difference between the excitation magnetic field and the resultant magnetic field. The method may comprise determining a calibration period and causing the calibration circuit to generate the calibration magnetic field during the calibration period. The calibration period may be a period between metal targets.

The calibration period may be determined according to an output from the one or more magnetometers. The calibration period may be determined based on the output from the one or more magnetometers absent the calibration magnetic field. The calibration period may be determined according to an input received from a production process.

According to an aspect of the invention there is provided a system for monitoring a microstructure of a metal target, comprising: a plurality of electromagnetic sensors for outputting a magnetic field, detecting a resultant magnetic field and outputting a detection signal in response thereto; and a control unit arranged to receive the detection signals from the plurality of electromagnetic sensors and to determine a microstructure of a metal target at the plurality of magnetic sensors.

The plurality of magnetic sensors may be arranged in a movement direction of the metal target. The plurality of magnetic sensors may be spaced apart in a cooling area of a production process of the metal target. The control unit may be arranged to determine a phase change between the output magnetic field and the resultant magnetic field for each of the plurality of magnetic sensors. The control unit may be arranged to determine a microstructure evolution of the metal target.

According to an aspect of the invention there is provided a production process comprising the system of an aspect of the invention wherein the control unit is arranged to output a signal indicative of the phase transformation of the metal target and one or more parameters of the production process are controlled in response thereto. The one or more parameters may be parameters of a process for cooling the metal target.

According to an aspect of the invention there is provided a method of monitoring a microstructure of a metal target, comprising: outputting a magnetic field at a plurality of electromagnetic sensors; detecting a resultant magnetic field at the plurality of magnetic sensors; and determining a microstructure of a metal target at each of the plurality of magnetic sensors.

The microstructure may be determined based upon a phase response of the resultant magnetic field with respect to the output magnetic field. The microstructure may be determined based upon a magnitude of the resultant magnetic field with respect to the output magnetic field. The method may comprise determining a microstructural rate of change of the metal target. The method may comprise varying one or more parameters of a production process in response to the determined microstructure. The one or more parameters may comprise cooling parameters of the metal target.

BRIEF DESCRIPTION OF THE DRAWINGS

Embodiments of the invention will now be described by way of example only, with reference to the accompanying figures, in which:

FIG. 1 is a schematic of a metal production process or "hot mill";

FIG. 2 is an illustration of a prior art electromagnetic sensor;

DETAILED DESCRIPTION OF EMBODIMENTS OF THE INVENTION

Figure 3:
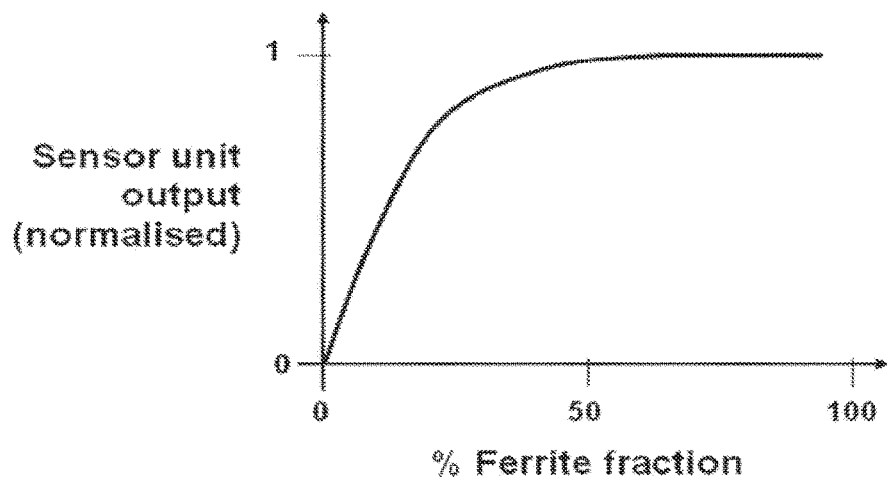
FIG. 3 is an example graph of normalised sensor output against ferrite fraction.

Embodiments of the present invention are intended to reduce problems associated with the monitoring of an evolution of a microstructure of a metal target during production processing of the metal target. An example of such processing may be in the case of steel production where hot rolling of the steel is followed by controlled cooling. However, it will be realised that embodiments of the present invention are not limited to use with steel targets and may be utilised with a range of metals, including ferrous and non-ferrous metal targets. Changes to the microstructure of the steel during the controlled cooling may be deduced by measurements of the accompanying electromagnetic properties of the material. Embodiments of the invention will be described with reference to the processing of steel. However, it is realised that embodiments of the invention may also be useful in monitoring other metals, particularly ferrous metals.

An overview of a metal processing stage, sometimes known as a "hot mill" is shown in FIG. 1.

Steel 101 being processed is rolled to a required shape and initial size with one or more successive passes through one or more rolling stands 110. The production process is typically instrumented with one or more sensors 120 to measure thickness, width, shape etc and temperature of the steel. When the steel product leaves the last rolling stand 110, the structure of the steel is usually a high-temperature face-centred cubic austenite phase.

As the steel cools, often in an accelerated cooling process with air, water or oil coolants which may be applied to the steel via one or a plurality of outlets 125 located in a controlled cooling zone, the steel transforms to a structure consisting of the body centred cubic ferrite phase and carbide, usually cementite (Fe3C), the morphology of the latter depending on cooling rate and composition. Increasing the cooling rate or alloy content causes transformation to occur at lower temperatures, giving a finer carbide dispersion and, hence, a stronger product. By altering the final microstructures, a wide range of strengths can be produced in the metal product from very low carbon, essentially, ferritic structures with tensile strengths of about 200 N/mm$^2$ to high strength steels with tensile strengths in excess of 1000 N/mm$^2$. These have higher carbon contents with microstructures consisting of mixtures of ferrite, pearlite, bainite, martensite and, in some cases, known as TRIP steels, austenite which by suitable alloying has been stabilized at temperatures down to ambient. The cooling process is often monitored and controlled by one or more temperature sensors 140, such as optical pyrometers, which may be positioned before and/or after and occasionally in special zones in the middle of the outlets 125.

It would be useful to monitor the structure of the steel during the cooling process, such as by sensors within the controlled cooling zone.

A number of techniques have been proposed for monitoring the steel microstructure on-line i.e. in real time, each with their limitations. Optical temperature sensors are used to implement feedback control of cooling but are adversely affected by water spray variations and surface emissivity irregularities. In addition, temperature is only an assumed indicator of microstructure and only the surface of the steel is measured. Other possible approaches such as X-ray diffraction and laser ultrasound have been demonstrated in the laboratory, but cannot easily be deployed in the water cooling zone due to the effects of water spray and mist.

Past attempts to use electromagnetic sensors to monitor microstructure have been limited by:

1) interference from other process parameters, such as the effects of nearby steelwork and variations in lift-off (i.e. the distance between the sensor head and the material)

2) a limited detection range, with the sensor response levelling off for ferritic phase fractions above typically 30% ferrite content. This is a serious limitation as the industry is interested in controlling transformation at much higher fractions
3) the difficulty of getting a sensor to work long-term in the hostile conditions encountered in a steel hot rolling mill especially with the effects of thermal drift because of the elevated temperatures that such sensors would have to endure.

FIG. 2 shows a prior art sensor unit, denoted generally with reference numeral 200, for detecting electromagnetic properties of a metal target 260.

Typically the metal target 260 may be moving quickly over a series of rollers and therefore close access to the metal target is restricted to one side only, with for instance a sensor unit 200 positioned between a pair of rollers.

The sensor unit 200 may contain a magnetic core 210, a magnetic excitation source 220 and one or more magnetic detectors 230, 240. The magnetic core 210 is configured to apply as much of an interrogating magnetic field 250 to the metal target 260 as possible and consequently designs based on U-shaped cores 210 are preferred. The excitation source 220 may be a permanent magnet or an electromagnet. The detection components 230, 240 are magnetometers and both induction detector coils and Hall probe sensor have been reported. The magnetic detectors 230, 240 are fitted to the poles of the magnetic core 210.

Also shown in FIG. 2 are two variations on the basic U-core design of sensor 200. The first variation shows an extra pole 270 and magnetometer, which may be added to provide an extra measurement of the magnetic field 250. The measurements provided by the extra magnetic detector 270 may be used to cancel potential sources of error, such as changes caused by the variation in the distance between the sensor unit 200 and the metal target 260. This distance is often referred to as lift-off. The second variation is the combination of two extra poles 280, 290 in a back-to-back configuration to realise an H-shaped sensor.

EP177626A entitled "System for Online-Detecting Transformation value and/or Flatness of Steel or Magnetic Material" discloses a system for detecting the transformation and/or a flatness of a steel or a magnetic material on-line. The system consists of an exciting coil on one side of the plate shaped metal target with an excitation coil generating an alternating magnetic field. Two or more detection coils are arranged at positions different in distance from the exciting coil but mutually induced with the exciting coil in an arrangement similar to that shown in FIG. 2. The magnetic measurements from the detection coils are fed to an arithmetic unit for obtaining the transformation value and the flatness of the metal target.

JP03262957A entitled "Transformation Ratio Measuring Instrument for Steel Material" discloses a system using separate magnetic cores of different sizes.

EP01308721 entitled "Device and Method for Detecting Magnetic Properties of a Metal Object" discloses a similar system to EP177626A, but in this case a device is disclosed for detecting the magnetic properties of a metal target object. The system comprises a means of generating a magnetic field and a detecting means for measuring the effect on a portion of the magnetic field produced by the metal target. In this case however, EP01308721 discloses that the generated magnetic field is a continuous DC magnetic field and the detecting means are means suitable for detecting at least a continuous component of the magnetic field. The detecting means may be positioned on the poles of the sensor unit as shown in FIG. 2. In addition the reported system has a non-magnetic metallic shield located between the generating and detection means and the metal target. The non-magnetic metallic shield does not affect the DC magnetic field, which is a key feature of using continuous DC rather than alternating AC magnetic fields.

To overcome problems associated with interference from the magnetisation of the rollers carrying the metal target when the metal target is in the form of a plate or strip, JP07325067A entitled "Transformation Factor Measuring Device" discloses a transformation factor measuring device in which the excitation source is provided in one side of a metal target plate and the detection components are provided in the other side of the metal target plate. This approach helps to reduce the effects of the magnetisation of the roller carrying the metal target plate, but has the disadvantages that different parts of the system are located in different positions making the system more difficult to deploy and making the system components more difficult to protect from the fast moving metal target plate.

A disadvantage of using a sensor unit which employs only a continuous DC excitation or a single frequency excitation is that the measurement system is sensitive a limited detection range of the transformed fraction of a steel target, with the sensor unit response levelling off for ferritic phase fractions above typically 30% ferrite content, as reported in (Yin et al, Journal of Material Science (2007), Vol. 42, pp. 6854-6861, "Exploring the relationship between ferrite fraction and morphology and the electromagnetic properties of steel") and as shown in FIG. 3. This is a serious limitation as the steel industry is interested in controlling transformation at much higher fractions. The paper by Yin et al discusses that a sensor unit can be used to identify the transformed fraction in steel targets across the full range (0-100%) of ferrite transformed fraction using multiple frequency measurements.

JP60017350A discloses a system to quantitatively measure the transformation rate of a steel target using an exciting coil and a detecting coil at the same side of the steel target to be measured, passing a current of variable frequency to the exciting coil, and obtaining a magnetic permeability of the measuring material for the thickness direction from both coils in each frequency.

The use of different frequencies has also been reported by (Dickinson et al, IEEE Transactions on Instrumentation and Measurement (2007), Vol. 56(3), pp. 879-886, "The development of a multi-frequency electromagnetic instrument for monitoring the phase transformation of hot strip steel"). This paper describes an instrument arranged to analyze the phase transformations of hot strip steel using an electromagnetic sensor. The sensor exploits variations in the electrical conductivity and magnetic permeability of the steel to monitor microstructure evolution during processing. The sensor is an inductive device based on an H-shaped ferrite core, which is interrogated with a multi-frequency impedance analyzer containing a digital signal processor. Online fast Fourier transform was performed to abstract the multi-frequency inductance changes due to the microstructural evolution of the sample. An overview of the instrument and measurements from a range of carbon steel samples are presented. The results verify the ability of the instrument both to monitor the microstructural changes and to reject variations in lift-off distance between the sensor and the hot strip.

JP 2000-304725 entitled "Method for Measuring Thickness of Transformation Layer of Steel Material" also discloses a multi-frequency method for monitoring the progress of transformation through a metal target. In this case the metal target is thick and the system measures the thickness of the outer transformed layer by analysing the spectra measured by the sensor unit.

However, significant problems exist with using such electromagnetic sensors in a metal processing environment. Some embodiments of the invention aim to reduce one or more of such problems so that electromagnetic sensors may be more reliably and accurately used in such environments. There are challenges for the design of an electromagnetic sensor unit. An ideal sensor unit should be able to (i) reject or reduce interference from other process parameters, such as the effects of nearby steelwork and variations in lift-off, (ii) measure a wide range of transformed fractions, such as a full range 0 to 100% of transformed fractions, and (iii) to have a low sensitivity to variations caused by the high temperature environment with hot metal at temperatures of 1000° C. only a short distance, such as a few cm from the active side of the sensor unit. Some embodiments of the invention may aim to address or reduce some of these problems.

A first aspect of an embodiment of the invention relates to an apparatus and method for calibrating an electromagnetic sensor unit. In particular, the first aspect relates to an apparatus and method for achieving regular calibration during operation of the sensor unit. Frequent calibration of the sensor unit is desirable because of the very high temperature environment encountered in operation with very high radiant heat loads, typically exerted at least in part from the metal target undergoing measurement.

Some embodiments of the invention provide an electronic means of applying one or more reference calibration levels to an electromagnetic sensor unit.

Figure 4:
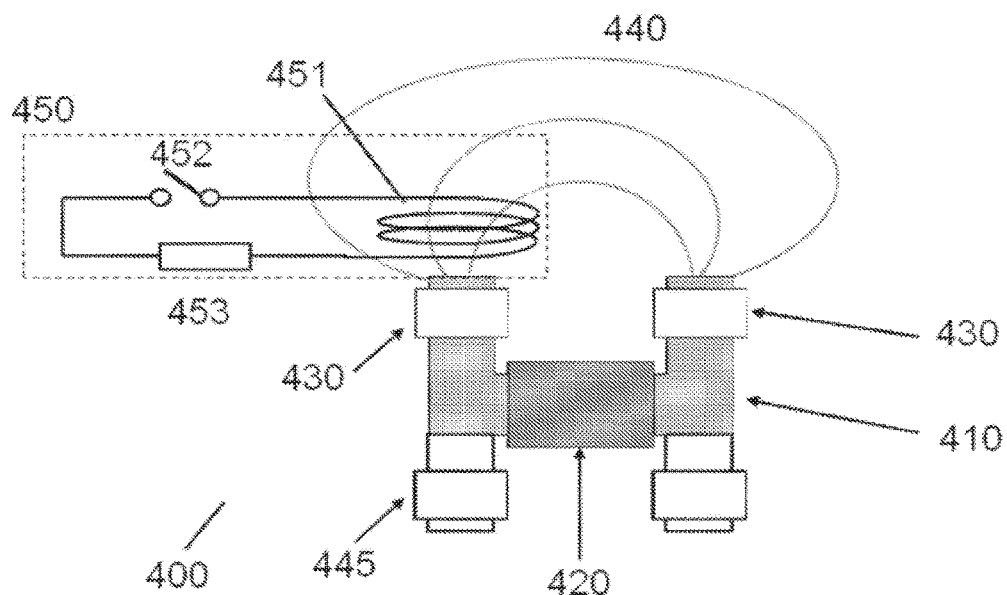
FIG. 4 is an illustration of an electromagnetic sensor according to a first embodiment of the invention.

FIG. 4 illustrates an apparatus 400 according to a first embodiment of the invention. The apparatus is an electromagnetic sensor unit 400 for sensing a microstructure of a metal target.

The sensor unit 400 comprises a magnetic core 410, one or more a magnetic excitation sources 420 and one or more magnetic detectors 430. The magnetic core 410 is configured to apply an interrogating magnetic field 440 generated by the excitation source(s) 420 to a metal target (not shown). The metal core 410 may be U-shaped, as shown in FIG. 4, or may be configured as a different shape, such as H-shaped. The excitation source 420 may be a permanent magnet, an electromagnet or a combination thereof. The magnetic detector 430 is arranged for detecting a magnetic field 440 and may include one or more induction detector coils and/or Hall probe sensors. Other magnetometers are also envisaged. In some embodiments, the sensor unit 400 comprises two magnetic detectors 430, each fitted to a corresponding pole of the magnetic core 410. The core 410 may be U-shaped or H-shaped (H-shaped includes two U-shaped cores arranged back-to-back). In some embodiments, the core may be H-shaped and comprises one or more background detector coils 445. The sensor unit 400 further comprises a calibration unit 450 for calibrating the sensor unit 400.

The calibration unit 450 comprises one or more calibration circuits for generating a calibration magnetic field which interacts with the magnetic field 440 generated by the one or more excitation sources 420 to simulate the effect of a metal target being present proximal to the sensor 400. In some embodiments of the invention, the calibration magnetic field is generated by currents induced in the calibration circuit by the interrogating magnetic field 440. The calibration circuit may comprise a calibration coil 451 for increasing the sensitivity of the calibration circuit to the magnetic field 440. Whilst one calibration coil 451 is shown in FIG. 4, it will be realised that the calibration unit 450 may comprise a plurality of calibration coils 451.

The calibration unit 450 may further comprise a control or switching means 452 for controlling an operation of the calibration coil 451. The control means 452 is shown in FIG. 4 as a switch for selectively activating the calibration coil 451 by selectively applying the induced electrical eddy current to the calibration coil 451. The control means may be operated responsive to a received calibration control signal, as will be discussed. In other embodiments, the control means 452 may be implemented in other ways, such as by a controllable power source or signal generator for selectively generating and applying a voltage or signal to the calibration coil 451. A reference impedance 453 or resistance may be provided in circuit with the calibration coil 451 for limiting a current flow through the calibration coil 451. Alternatively, a current limited output from a power supply or signal generator may be used. Although not shown in FIG. 4, a power source may be included in the calibration unit 450 for providing an electrical current or signal for the calibration coil 451, which is selectively applied via the switch 452.

Each calibration coil 451 may be positioned around a pole of the magnetic core 410 so as to interact with a portion of the magnetic flux 440 generated by the excitation source 420 which would be applied to the metal target.

When the switch 452 is closed, an electrical current is able to flow around the calibration circuit containing the calibration coil 451 and reference impedance 453.

The calibration unit 450 has an effect on the magnetic sensor similar to that of the flow of the eddy currents that would be induced in the metal target by the excitation source 420. Consequently the calibration unit 450 can provide a known input to the sensor unit 400 which may be used to calibrate the sensor unit 400. The calibration unit 450 may be activated manually, such as by user activation of the switch 452, or automatically i.e. by the switch 452, power source or signal generator being activated by a control unit, such as a microprocessor or the like.

Figure 5:
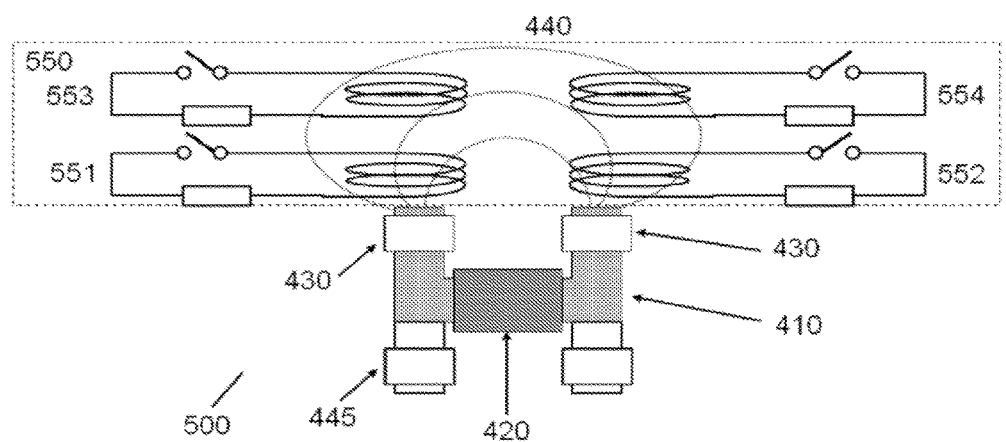
FIG. 5 is an illustration of an electromagnetic sensor according to a second embodiment of the invention.

FIG. 5 illustrates an apparatus 500 according to a further embodiment of the invention. The apparatus 500 comprises an electromagnetic sensor 410, 420, 430, 440, 445 as previously described with reference to FIG. 4 and a repeated discussion of like numbered parts will be omitted for clarity. The apparatus 500 further includes a calibration unit 550 having a plurality of calibration circuits 551, 552, 553, 554. Each calibration circuit 551, 552, 553, 554 may each be considered to be a calibration unit 450 as previously described with reference to FIG. 4, and repeat discussion will again be omitted for clarity. As discussed previously, each calibration circuit 551, 552, 553, 554 may include one or more calibration coils.

Each of the calibration circuits 551, 552, 553, 554 may be individually controlled to generate a corresponding magnetic field. Each calibration coil may be configured to operate within a different respective calibration frequency range to calibrate the response of the sensor unit 500 at each frequency range. A first calibration coil 551 may be configured to operate within a first calibration frequency range, which is a relatively low frequency range. The configuration may include providing the first calibration coil 551 with one or relatively few turns. Similarly, the reference impedance associated with the first calibration coil 551 may be relatively low. A fourth calibration coil 554 may be configured to operate within a fourth frequency range, which is a relatively high calibration frequency range. The configuration may include providing the fourth calibration coil 554 with a relatively large number of turns. Second and third calibration coils 552, 553 may be configured to operate within second and third respective calibration frequency ranges, which may be equally or unequally spaced between the first and fourth calibration frequency ranges. Whilst the second embodiment is shown having four calibration circuits 551, 552, 553, 554, it will be realised that more or less calibration circuits may be provided.

Figure 6:
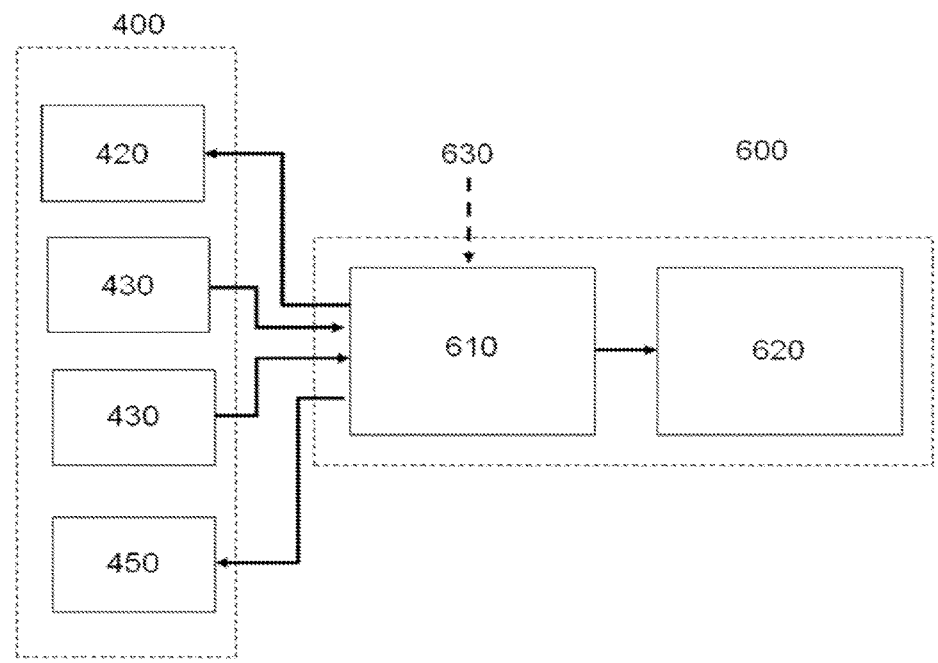
FIG. 6 is a schematic of a system according to an embodiment of the invention.

FIG. 6 illustrates a system 600 according to an embodiment of the invention. The system 600 is arranged for sensing the microstructure of a metal target, such as steel being formed in a production process, such as a hot mill.

The system 600 comprises an electromagnetic sensor unit 400 as shown in FIG. 4 and a control unit 600. Embodiments of the system 600 may also be envisaged which include the sensor unit 500 of FIG. 5. In which case, the control unit 600 may have a plurality, such as four, calibration control signals of different frequency provided to the four calibration coils.

The control unit 600 comprises a signal unit 610 for generating excitation and control signals and receiving detection signals for/from the sensor unit 400, respectively. In particular, the signal unit 610 may output one or more excitation signals to the excitation coil 420 of the sensor unit 400, and may receive detection signals from one or more detection coils 430 of the sensor unit 400 (the embodiment shown in FIG. 6 comprises an excitation signal provided to an excitation coil 420 and two detection coils 430, although other numbers of excitation coils and detection coils may be envisaged). The signal unit 610 is further arranged to output a calibration control signal to the calibration unit 450 to be received by the control means 452 for controlling the operation of the calibration circuit. The control unit 600 may further comprise a signal processing unit 620 for processing detection signals received from the sensor unit 400, as will be explained.

In order to calibrate the sensor unit 400, the control unit 600 generates an excitation signal for the excitation coil 420 of the sensor unit 400. The excitation signal may be a time-variant waveform, such as a sine or cosine waveform. The excitation signal may comprise waveforms summed together to form a multi-frequency waveform. Such waveforms are described in Dickinson et al, IEEE Transactions on Instrumentation and Measurement (2007), Vol. 56(3), pp. 879-886, which is herein incorporated by reference, although other waveforms may be used. A driver circuit, although not shown in FIG. 6, may be arranged between the output of the signal unit 610 and the one or more excitation coils 420. The control unit 600 also generates a calibration control signal for the calibration unit 450. The calibration control signal may control the switch 452, such that a circuit is selectively formed which includes the calibration coil 451, or may directly generate a calibration signal applied to the calibration coil, such as a signal having a frequency f. As a result, a calibration magnetic field is generated. The calibration field effectively modifies the magnetic flux generated by the excitation coil 420 to produce a known effect on the sensor 400, which is similar to that of the metal target. The calibration field imitates a flow of eddy currents that would be induced in the metal target by the excitation signal. The control unit 600 is further arranged to receive one or more detector signals from the detection coils 430. The signal unit 610 may digitise each of the received signals and communicate information indicative of the received signals and of the generated excitation signal to the signal processing unit 620.

Figure 7:
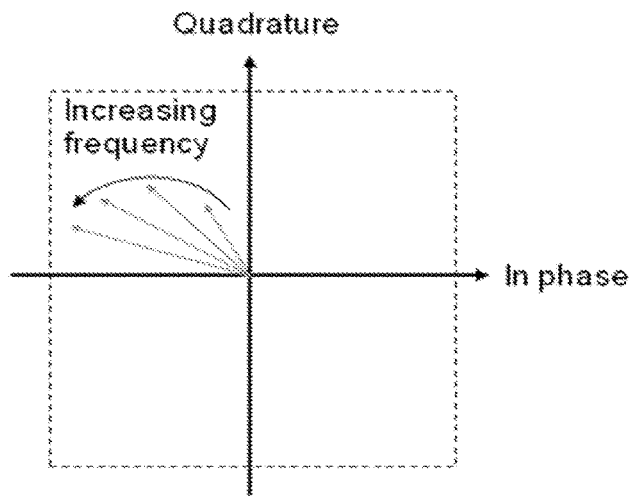
FIG. 7 is an illustration of phasors determined at a plurality of signal frequencies.

Based on the information received from the signal unit 610, the signal processing unit 620 converts the digitised signals into phasor equivalents using down conversion techniques as will be appreciated, such as from the cited references. The signal processing unit 620 is arranged to determine impedance change in the electromagnetic sensor 500 resulting from the metal target or the calibration field, as will be appreciated by those skilled in the art. The impedance change is determined having real and imaginary components i.e. as quadrate and in-phase components, as shown in FIG. 7. These may be determined by the signal processing unit 620 comparing the excitation coil 420 current and detection coil 430 output voltage waveforms. This may be performed at each of a plurality of frequencies of interest, particularly to obtain a depth-dependent profile since higher frequency signals penetrate more deeply into the metal target. The complex impedance at each frequency may be calculated by the signal processing unit applying Fast Fourier Transforms (FFTs) to the voltage and current waveforms to obtain the phase and magnitude of the respective signals at each separate frequency. An example of multi-frequency measurements is shown in FIG. 7 for a non-magnetic metal target and similar multi-frequency measurements may be obtained with the application of the calibration coil arrangement 450, shown in FIG. 4.

To calibrate the electromagnetic sensor 400, the signal processing unit 620 is arranged to determine a gradient or sensitivity of the electromagnetic sensor 620 to the output of the calibration unit 450, 550 at one or more frequencies of interest by subtracting a response of the one or more detector coils 430 in the absence of a metal target or output of the calibration unit 450 (a background level) from a response of the detector coils 430 in the absence of a metal target but with the calibration unit 450, 550 generating a known calibration signal.

The operation of the calibration unit may be described as follows. Here complex phasor notation is used to describe the response the sensor. Let, $Z_{0fn}$ be the complex impedance output of the sensor when no metal target is present and the calibration circuit is not activated at frequency $f_n$, and $Z_{Cfn}$ be the complex impedance output of the sensor when no metal target is present and the calibration coil is activated, at frequency $f_n$, and $Z_{fn}$ be the complex impedance output of the sensor when the metal target is present and the calibration coil is not activated, at frequency $f_n$. The normalised and calibrated sensor output, $N_{Nfn}$ can be calculated as follows:

$$N_{Nfn} = \frac{Z_{fn} - Z_{0fn}}{Z_{Cfn} - Z_{0fn}}$$

Finally, the calibrated sensor output $Z_{Afn}$ at frequency $f_n$ can further be calculated as $$Z_{Afn} = k \cdot N_{Nfn}$$

where k is a complex scaling factor relating the response of the calibration circuit at frequency $f_n$ to the ideal response at this frequency.

Figure 8:
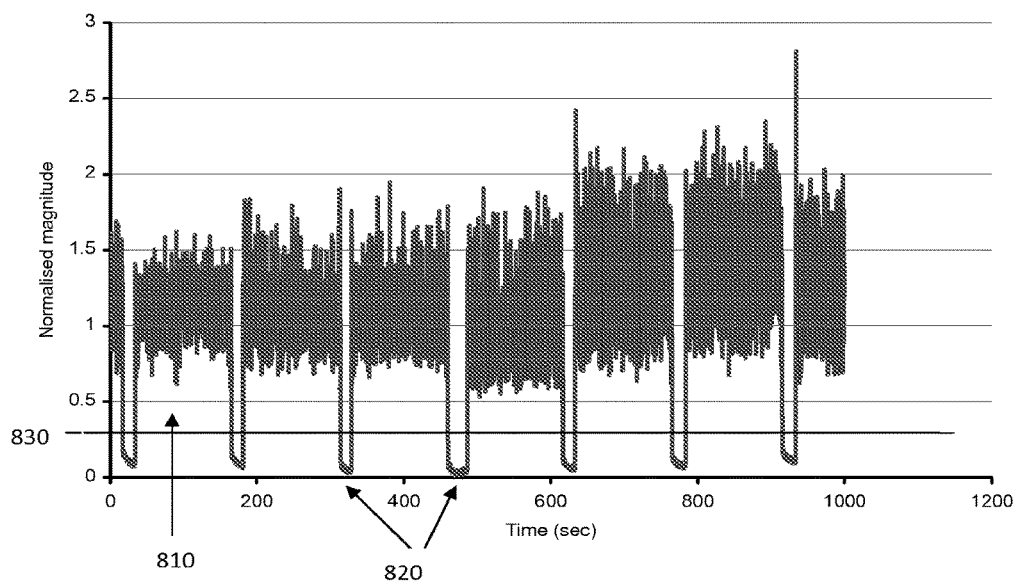
FIG. 8 is an example of a sensor output according to an embodiment of the invention.

Some embodiments of the invention exploit a time interval between metal targets i.e. when no metal target is proximal to the electromagnetic sensor, to calibrate the electromagnetic sensor. The time interval, typically a few seconds or more, that occurs on metal production processes, such as hot mills, between rolling operations on each metal slab, bloom or billet to the final product such as strip, plate, medium sections, rail, rod etc, as shown in FIG. 8. FIG. 8 illustrates an example output from an electromagnetic sensor 400, 500 arranged to monitor metal targets produced from a hot mill. Reference numeral 810 denotes an output level when a metal target is present proximal to the sensor 400, 500, whereas 820 denotes an output level when a metal target is not proximal to the sensor i.e. the sensor unit is located between successive metal targets and its output is relatively low. It has been realised that a time interval 820 between metal targets may, in some embodiments, present an opportunity to apply one or more known input conditions to a sensor unit to calibrate that sensor unit. A predetermined threshold level 830 may be utilised to by the control unit 600 to determine when the metal target is not proximal to the sensor.

In order to calibrate the sensor 400, 500 both zero (background) and a predetermined reference level may be applied to the sensor unit 400, 500. The zero reference level may be obtained directly during the time interval between rolling operations when no material is present i.e. with no output from the calibration coil. The predetermined reference level corresponds to an output from the one or more calibration coils. In the prior art, this has been achieved by positioning a reference sample of material with known electromagnetic properties proximal to the sensor unit. However, this is difficult or inconvenient to achieve in a short period of time and/or on a regular basis, such as between metal targets being produced by a hot mill.

Figure 9:
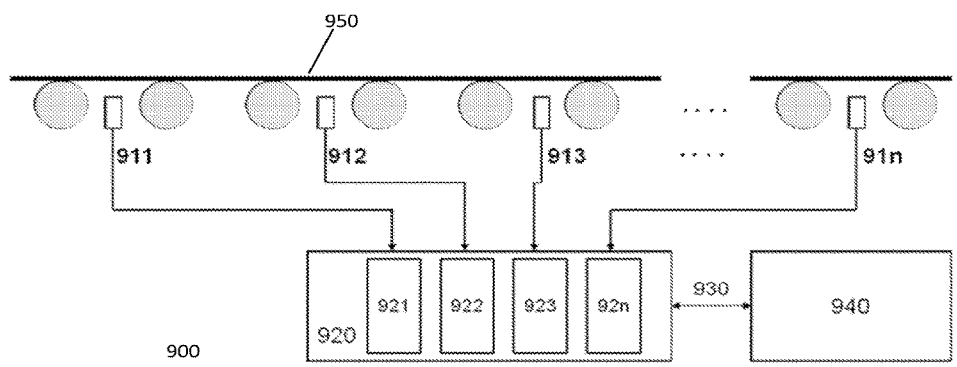
FIG. 9 is an apparatus according to a further embodiment of the invention.

FIG. 9 illustrates an apparatus 900 according to a further embodiment of the invention. The apparatus 900 is arranged to determine a time-dependent profile of the electromagnetic properties of a metal target 950. In particular, the apparatus 900 may be utilised to determine or to monitor the evolution of the electromagnetic properties of the metal target 950 as it cools following a hot production process, such as hot rolling.

The apparatus 900 includes a plurality of electromagnetic sensors 911, 912, 913 . . . 91*n*. Each electromagnetic sensor 911, 912, 913 . . . 91*n* may be as described previously with reference to FIG. 4 or 5. However, it will be appreciated that each electromagnetic sensor 911, 912, 913 . . . 91*n* may not comprise a calibration unit 450, 550. That is, some embodiments of the invention include electromagnetic sensors which do not comprise a calibration unit or circuit, although it will be realised that embodiments may be envisaged which do.

The system 900 further comprises a plurality of control units 921, 922, 923, 92*n*, each associated with a respective electromagnetic sensor 911, 912, 913 . . . 91*n* for determining a phase response of the respective electromagnetic sensor 913 . . . 91*n* to the metal target. The control units may be individually formed i.e. separately arranged to each provide an output to a monitoring system, or may be arranged as shown in FIG. 9 where each control unit is a component part of a control system 920. When combinedly formed, as shown in FIG. 9, it may be possible to reduce an overall number of components via re-use of some sub-systems. The control units 921, 922, 923, 92*n* may be as shown in and described with reference to FIG. 6.

However, each control units 921, 922, 923, 92*n* may not comprise an output for controlling a calibration unit 450, 550. Each control unit 921, 922, 923, 92*n* may comprise one or more excitation signal outputs and one or more detector signal inputs for determining the phase response of the electromagnetic sensor when proximal to the metal target. Each control unit 921, 922, 923, 92*n* is arranged to determine a change in structure of the metal target utilising the respective electromagnetic sensor 911, 912, 913 . . . 91*n*.

Figure 10:
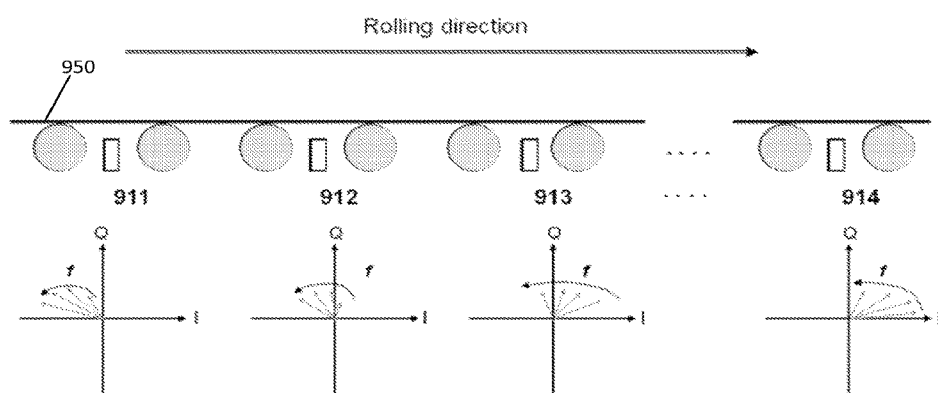
FIG. 10 is an illustration of phasors determined from a plurality of sensors according to embodiments of the invention.

The electromagnetic sensors 911, 912, 913 . . . 91*n* may be arranged proximal to a path of the metal target through one or more cooling zones, as explained above. The cooling zones may include means for controllably cooling the metal target. The means for controllably cooling the metal target may include one or more means for applying a fluid to the metal target, such as air or other gasses or liquids, such as water or oil. As the metal target is moved in a rolling direction (shown in FIG. 10) it moved past a first electromagnetic sensor 911. Responsive to an excitation signal generated by the respective control unit 921, one or more detection signals are received. The excitation signal may include a plurality of frequency components, as indicated in FIG. 10, although the presence of these multi-frequency components and the number thereof is not limiting. The first control unit 921 is arranged to determine a phase response of the electromagnetic sensor at each frequency of the excitation signal. Similarly, as the metal target progresses past each of the second, third and fourth electromagnetic sensors 912, 913, 914, the respective control unit is arranged to determine the sensor response at each frequency of excitation signal and the associated phase response, as shown in FIG. 10.

It can be observed in FIG. 10, although the phase diagrams for each sensor are merely for illustration and are not to scale, that the four illustrated phasors are gradually rotated clockwise indicating the development or evolution of the structure of the metal target as it cools. The control system 920 may therefore determine the structural development of the metal target in real time. Based on the determined developmental rate, the control system 920 may be arranged to output a signal 930 indicative of the structural development to a processor controller 940 arranged to control the metal production process. The signal may indicate a deviation of the structural development of the metal target from a predetermined structural development rate, such that the process controller 940 may vary one or more parameters of the production process to optimise the structural development of the metal target. For example, if the signal 930 indicates that the structure of the metal target is forming as a result of cooling more quickly than desired, the process controller may reduce a rate of fluid flow toward the metal target, such as by reducing a water flow rate from outlets 125 described above. In this way, the cooling of the metal target may be slowed to a desired rate. In this way, the resulting qualities of the metal target may be controlled by real time monitoring of the structural changes of the metal target.

It will be appreciated from the discussion above that some embodiments of the invention allow convenient calibration of electromagnetic sensors. In particular, in some embodiments, the calibration may be performed in an automatically determined period between metal targets. In some embodiments, an array of electromagnetic sensors is utilised to determine an evolution of a microstructure of a metal target. By such monitoring, properties of the metal target may be controlled.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A system for monitoring a microstructure of a metal target, comprising:
    a plurality of electromagnetic sensors for outputting a magnetic field, wherein an excitation signal output by each of the electromagnetic sensors is a multi-frequency waveform, detecting a resultant magnetic field and outputting a detection signal in response thereto; and
    a control unit arranged to receive the detection signals from the plurality of electromagnetic sensors, to determine a phase change between the output magnetic field and the resultant magnetic field at each of a plurality of frequencies forming the multi-frequency waveform for each of the plurality of electromagnetic sensors, to determine a microstructure development rate of a metal target at the plurality of electromagnetic sensors based on the phase changes, and to determine a deviation of the microstructure development rate from a predetermined microstructure development rate.

2. The system of claim 1, wherein the plurality of electromagnetic sensors are arranged in a movement direction of the metal target.

3. The system of claim 1, wherein the control unit is arranged to determine a microstructure evolution of the metal target.

4. A production process comprising the system of claim 1, wherein the control unit is arranged to output a signal indicative of the deviation of the microstructure development rate of the metal target, the production process comprising a processor for controlling the production process, wherein the processor is arranged to receive the signal indicative of the deviation and to control one or more parameters of the production process in response thereto.

5. The production process of claim 4, wherein the one or more parameters are parameters of a process for cooling the metal target.

6. The system of claim 5, wherein the plurality of electromagnetic sensors is spaced apart in a cooling area of a production process of the metal target.

7. A method of monitoring a microstructure of a metal target, comprising:
    outputting a magnetic field generated in response to a multi-frequency waveform at a plurality of electromagnetic sensors
    detecting a resultant magnetic field at the plurality of electromagnetic sensors;
    determining a phase response of the resultant magnetic field with respect to the output magnetic field at each of a plurality of frequencies forming the multi-frequency waveform; and
    determining a microstructure development rate of a metal target at each of the plurality of electromagnetic sensors based upon the phase response; and
    determining a deviation of the microstructure development rate from a predetermined microstructure development rate.

8. The method of claim 7, wherein the microstructure is determined based further upon a magnitude of the resultant magnetic field with respect to the output magnetic field.

9. The method of claim 7, comprising determining a microstructural rate of change of the metal target.

10. The method of claim 7, comprising varying one or more parameters of a production process in response to the determined microstructure.

11. The method of claim 10, wherein the one or more parameters comprise cooling parameters of the metal target.

* * * * *